United States Patent
Horiba et al.

(10) Patent No.: US 7,041,264 B2
(45) Date of Patent: May 9, 2006

(54) PROCESS FOR PURIFYING OCTAFLUOROPROPANE

(75) Inventors: Minako Horiba, Kawasaki (JP); Yasuhiro Suzuki, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 565 days.

(21) Appl. No.: 10/221,447

(22) PCT Filed: Jan. 11, 2002

(86) PCT No.: PCT/JP02/00147

§ 371 (c)(1), (2), (4) Date: Sep. 12, 2002

(87) PCT Pub. No.: WO02/055457

PCT Pub. Date: Jul. 18, 2002

(65) Prior Publication Data

US 2004/0047785 A1 Mar. 11, 2004

Related U.S. Application Data

(60) Provisional application No. 60/264,320, filed on Jan. 29, 2001.

(30) Foreign Application Priority Data

Jan. 15, 2001 (JP) .......................................... 2001-6458

(51) Int. Cl.
 *C01B 17/20* (2006.01)

(52) U.S. Cl. ................................. 423/240 S; 423/245.3

(58) Field of Classification Search ............. 423/240 R, 423/240 S, 245.1, 245.3, 414, 439, 462, 489; 570/177, 179
See application file for complete search history.

(56) References Cited

U.S. PATENT DOCUMENTS 5,675,046 A * 10/1997 Ohno et al. .................. 570/134
6,187,077 B1 * 2/2001 Li ................................ 95/47
6,720,464 B1 * 4/2004 Ohno et al. .................. 570/169

FOREIGN PATENT DOCUMENTS

| DE | 27 12 732 A1 | 9/1978 |
|----|----|----|
| EP | 0 370 688 A1 | 5/1990 |
| EP | 0 457 613 A1 | 11/1991 |
| EP | 0 537 760 A2 | 4/1993 |
| EP | 0 733 612 A1 | 9/1996 |
| GB | 1 568 020 | 5/1980 |
| JP | 60-77983 A | 5/1985 |
| JP | 60-81134 A | 5/1985 |
| JP | 62-61572 B2 | 12/1987 |
| JP | 1-45455 B2 | 10/1989 |
| RU | 2041194 C1 | 8/1995 |
| RU | 2100339 C1 | 12/1997 |

OTHER PUBLICATIONS

V.B. Maksimov et al, Industrial Organofluoric Products, Khimiya Publishers, St. Petersburg, 1996, pp. 30–36, no month.

English Abstract for JPA 58–041829 (Mar. 11, 1983) corresponding to JPB 62–61572.

English Abstract for JPA 60–078924 (May 4, 1985) corresponding to JPB 1–45455.

* cited by examiner

*Primary Examiner*—Edward M. Johnson
(74) *Attorney, Agent, or Firm*—Sughrue Mion, PLLC

(57) ABSTRACT

A process for purifying octafluoropropane according to the present invention includes the step of contacting a crude octafluoropropane containing impurities with an impurity decomposing agent under an elevated temperature and then with an adsorbent to substantially remove the impurities from the crude octafluoropropane. According to the purification process or preparation process of octafluoropropane of the present invention, impurities such as chlorine compounds can be substantially removed and a high-purity octafluoropropane can be easily obtained. The octafluoropropane obtained by the purification process of the present invention is substantially free of impurities and, therefore, can be used as an etching or cleaning gas for use in the production process of a semiconductor device and the like.

15 Claims, No Drawings

PROCESS FOR PURIFYING OCTAFLUOROPROPANE

CROSS REFERENCE OF RELATED APPLICATION

This application is an application filed under 35 U.S.C. §111(a) claiming benefit pursuant to 35 U.S.C. §119(e)(1) of the filing date of Provisional Application No. 60/264,320 filed on Jan. 29, 2001, pursuant to 35 U.S.C. §111(b).

TECHNICAL FIELD

The present invention relates to a process for purifying an octafluoropropane, a process for preparing a high-purity octafluoropropane, a high-purity octafluoro-propane, and uses thereof.

BACKGROUND ART

Heretofore, in the process of producing semiconductor devices, a gas etching for partially removing a thin-film material is performed for forming a circuit pattern on various thin-film materials constituting a semiconductor circuit and at the same time, removal of deposits using a cleaning gas is performed to remove a thin-film starting material deposited to the reactor during the thin film formation. One of useful etching gases or cleaning gases conventional for the production process of a semiconductor device is octafluoropropane (hereinafter referred to as "FC-218").

On the other hand, to keep up with recent tendency toward higher performance, smaller size, higher density wiring of electrical or electronic equipment, the circuit patterns are becoming finer and in order to form a higher-precision circuit pattern by etching, use of a high-purity etching gas from which impurities are eliminated as much as possible is demanded. When an etching gas contains an impurity even a very small amount, this may cause generation of a large width line during the formation of a fine pattern and increase of defects in the product having a high density integrated circuit.

Also in the process of removing deposits using a cleaning gas, residual impurities in the production process of a semiconductor device after cleaning must be reduced as much as possible so as to provide a high-purity and high-quality device. For this purpose, a high-purity cleaning gas containing substantially no impurity is demanded.

With respect to the production process of FC-218, for example, a method of electrolytically fluorinating 1-chloropropane (see, U.S. Pat. No. 3,709,800), a method of reacting trifluoropentachloropropane with manganese trifluoride (see, U.S. Pat. No. 2,578,721) and a method of reacting hydrogen fluoride and chlorine with compounds such as propane and propylene (see, U.S. Pat. No. 5,220,083) are known. However, in these methods, a compound containing chlorine is used as a starting material and therefore, a chlorine-containing compound is produced as a by-product and mixed into FC-218 as impurities.

On the other hand, with respect to the method of producing FC-218 using chlorine-free starting materials, for example, a method of electrolytically fluorinating propane is known (see, U.S. Pat. No. 3,840,445). However, these methods are industrially disadvantageous because the apparatus therefor is very complicated and the yield is low.

In addition, a method of fluorinating hexafluoropropene (hereinafter sometimes referred to as "FC-1216") to produce FC-218 is known. For example, a method of reacting FC-1216 with a fluorine gas under dilution with an inert gas and a reaction product gas, a method of electrolytically fluorinating FC-1216 in hydrogen fluoride (see, JP-B-62-61115) (the term "JP-B" as used herein means an "examined Japanese patent publication"), and a method of reacting at least one high-valence metal fluoride selected from cobalt trifluoride, manganese trifluoride and silver difluoride with FC-1216 (see, JP-B-62-54777) are known.

In this case, to produce FC-1216, for example, a process comprising thermal decomposition of chlorodifluoromethane (hereinafter sometimes referred to as "HCFC-22") and a process comprising fluorinating perhalogenated chlorofluorocarbon having 3 carbon atoms and then dehalogenating the fluorination product to produce FC-1216 (see, U.S. Pat. No. 5,057,634) are known.

However, also in these methods, a chlorine-containing compound is usually used as a starting material and therefore, the obtained FC-1216 usually contains a chlorine-containing compound as impurities. As a result, FC-218 produced starting from this FC-1216 contains the chlorine-containing compound together with unreacted FC-1216.

Accordingly, these chlorine-containing compound and fluorocarbon impurities such as FC-1216 must be removed from FC-218.

For example, separation of these impurities from FC-218 by distillation or the like is attempted. More specifically, impurities contained in FC-218 can be theoretically removed by distillation if these have a boiling point different from that of FC-218. However, as shown in Table 1 below, chloropentafluoroethane, (hereinafter sometimes referred to as "CFC-115"), FC-1216, dichlorodifluoromethane (hereinafter sometimes referred to as "CFC-12") and HCFC-22, which are mixed in many cases as impurities, each has a boiling point approximated to the boiling point of FC-218. Therefore, it is very difficult to separate these impurities by distillation and obtain high-purity FC-218.

TABLE 1

| Compound Name | Structural Formula | Boiling Point (° C.) |
|---|---|---|
| Octafluoropropane (FC-218) | $CF_3CF_2CF_3$ | −36.7 |
| Chloropentafluoroethane (CFC-115) | $CClF_2CF_3$ | −38.7 |
| Hexafluoropropene (FC-1216) | $CF_3CF{=}CF_2$ | −31 |
| Dichlorodifluoromethane (CFC-12) | $CCl_2F_2$ | −29.8 |
| Chlorodifluoromethane (HCFC-22) | $CHClF_2$ | −41 |

Therefore, a purification method other than the separation by distillation, such as extractive distillation, membrane separation and adsorption separation, is being attempted.

However, the extractive distillation method has a problem in that the equipment costs highly and the process is cumbersome. The membrane separation method has a problem in that an appropriate and practical membrane having properties necessary for separating FC-218 from impurities is not known, and purification to high purity, for example, such that the content of impurities in FC-218 is 1 ppm by mass or less, is difficult.

Also, as shown in Table 2, there is almost no difference in the molecular size (calculated value at stable state structure) between FC-218 and CFC-115 or FC-1216, there is no difference in the boiling point between FC-218 and impurities, and FC-218 and impurities are approximated in the structure and physical properties. Therefore, purification to a high purity by the removal of impurities cannot be attained by an adsorption separation method using a known adsorbent such as activated carbon, silica gel, zeolite (molecular sieves) and molecular sieving carbon (hereinafter referred to as "MSC").

TABLE 2

| Compound Name | Molecular Size (calculated value) |
| --- | --- |
| Octafluoropropane (FC-218) | 4.9 to 6.1 Å |
| Chloropentafluoroethane (CFC-115) | 4.3 to 5.6 Å |
| Hexafluoropropene (FC-1216) | 4.9 to 5.9 Å |

Among these, FC-1216 which is one of impurities can be removed by adsorption using activated carbon or MSC, however, chlorine-containing compounds such as CFC-115 cannot be separated.

Accordingly, in conventional purification methods, it is difficult to obtain high-purity FC-218 by reducing the concentration of fluorocarbon impurities including chlorine compounds such as CFC-115 to less than 1 ppm by mass.

As a result of extensive investigations to solve these problems, the present inventors have found that when crude octafluoropropane containing impurities such as chlorine compounds is contacted with an impurity decomposing agent containing an iron oxide and an alkaline earth metal compound and then with an adsorbent, these impurities can be substantially removed with ease.

More specifically, the present inventors have found a purification process of FC-218, where FC-218 containing fluorocarbon impurities such as CFC-115, FC-1216, CFC-12, CFC-13 (chlorotrifluoromethane) and HCFC-22 in a concentration of 10 to 10,000 ppm by mass is contacted with an impurity decomposing agent and further with an adsorbent and thereby these impurities can be reduced to less than 1 ppm by mass. The present invention has been accomplished based on this finding.

OBJECT OF THE INVENTION

An object of the present invention is to solve the above-described problems in conventional techniques and provide a process for purifying an octafluoropropane, where impurities can be substantially removed from a crude octafluoropropane containing impurities.

Another object of the present invention is to provide a process for preparing an octafluoropropane, comprising the above-described purification steps, and also provide a high-purity octafluoropropane and uses thereof.

SUMMARY OF THE INVENTION

The process for purifying an octafluoropropane according to the present invention is characterized in that a crude octafluoropropane containing impurities is contacted with an impurity decomposing agent under elevated temperature (heating) and then with an adsorbent to substantially remove the impurities from the crude octafluoropropane.

The impurity decomposing agent preferably comprises an iron oxide and an alkaline earth metal compound.

The iron oxide is preferably a ferric oxide and the ferric oxide is preferably a γ-iron hydroxide oxide and/or a γ-ferric oxide.

The alkaline earth metal compound is preferably at least one compound selected from the group consisting of oxides, hydroxides and carbonates of an alkaline earth metal of magnesium, calcium, strontium or barium.

The impurity decomposing agent preferably contains from 5 to 40% by mass of an iron oxide and from 60 to 95% by mass of an alkaline earth metal compound, based on the entire mass of the impurity decomposing agent.

The impurity decomposing agent is preferably a granule comprising a powder of the iron oxide having an average particle size of 100 μm or less and a powder of the alkaline earth metal having an average particle size of 100 μm or less.

The impurity decomposing agent is preferably a granule having an average particle size of 0.5 to 10 mm.

The crude octafluoropropane is preferably contacted with the impurity decomposing agent at a temperature of 250 to 380° C.

The adsorbent is preferably at least one member selected from the group consisting of activated carbon, molecular sieve and molecular sieving carbon.

The crude octafluoropropane may contain the impurities in an amount of 10 to 10,000 ppm by mass.

The impurity is preferably at least one compound selected from the group consisting of chloropentafluoroethane, hexafluoropropene, chlorotrifluoromethane, dichlorodifluoromethane and chlorodifluoromethane.

After the impurities are substantially removed, the concentration of impurities remaining in the octafluoropropane can be less than 1 ppm by mass.

The process for preparing an octafluoropropane according to the present invention is characterized by comprising the steps of producing a crude octafluoropropane containing impurities, and contacting the crude octafluoropropane with an impurity decomposing agent under heating and then with an adsorbent to obtain an octafluoropropane from which impurities are substantially removed.

The step of producing a crude octafluoropropane containing impurities may be the fluorination of hexafluoropropene. Also, the impurity may be at least one compound selected from the group consisting of chloropentafluoroethane, hexafluoropropene, chlorotrifluoromethane, dichlorodifluoromethane and chlorodifluoromethane.

The octafluoropropane according to the present invention is characterized by containing less than 0.0001% by mass of a chlorine compound and having a purity of 99.9999% by mass or more.

The gas according to the present invention is characterized by comprising the above-described octafluoro-propane.

The etching gas according to the present invention is characterized by comprising the above-described gas.

The cleaning gas according to the present invention is characterized by comprising the above-described gas.

DETAILED DESCRIPTION OF INVENTION

[Purification Process]

The process for purifying an octafluoropropane according to the present invention comprises the step of contacting a crude octafluoropropane containing impurities with an impurity decomposing agent under heating (elevated temperature) and then with an adsorbent to substantially remove the impurities from the crude octafluoropropane. This purification process is described below in detail. The "crude octafluoropropane" as used in the present invention means an octafluoropropane containing impurities, which is not passed through a purification step in the present invention. Also, the "substantially remove" as used herein means that absolutely no impurities or almost no impurities are contained.

Impurity Decomposing Agent

In the present invention, an impurity decomposing agent comprising an iron oxide and an alkaline earth metal compound is preferably used.

Examples of the iron oxide include ferrous oxide and ferric oxide. Among these, ferric oxide is preferred. Among ferric oxides, γ-FeOOH (γ-iron hydroxide oxide) and γ-Fe$_2$O$_3$ (γ-ferric oxide) are preferred, and γ-FeOOH is more preferred.

These iron oxides can be used individually or in combination of a plurality of iron oxides.

The reason why γ-FeOOH and γ-Fe$_2$O$_3$ are preferred as compared with α-Fe$_2$O$_3$ is considered to have relation to the activity of iron oxide. The γ-FeOOH and γ-Fe$_2$O$_3$ are higher in the reactivity and the activity with chlorine compound is in the order of γ-FeOOH>γ-Fe$_2$O$_3$>α-FeOOH>Fe$_2$O$_3$>>α-Fe$_2$O$_3$. This difference in the activity with chlorine compound is presumed because the bonding energy between an iron atom and an oxygen atom in the γ-FeOOH or γ-Fe$_2$O$_3$ is lower than that in α-FeOOH.

The alkaline earth metal compound for use in the present invention is preferably a hydroxide, an oxide or a carbonate of an alkaline earth metal. Example of the alkaline earth metal include magnesium, calcium, strontium and barium.

Among these alkaline earth metal compounds, a hydroxide or an oxide of calcium is preferably used, and calcium hydroxide is more preferred. These alkaline earth metal compounds can be used individually or in combination of a plurality of alkaline earth metal compounds.

The impurity decomposing agent for use in the present invention preferably contains the iron oxide and the alkaline earth metal compound such that an amount of iron oxide is from 5 to 40% by mass, preferably from 20 to 30% by mass, and an amount of the alkaline earth metal compound is from 60 to 95% by mass, preferably from 70 to 80% by mass, respectively, based on the entire mass of the impurity decomposing agent.

It is presumed that when the amounts of the iron oxide and the alkaline earth metal compound contained in the impurity decomposing agent fall within the above-described range, the decomposition of impurities and the removal of the decomposition products can be effectively performed as described later, whereby efficient purification can be performed by using the characteristic features of the iron oxide and the alkaline earth metal compound.

A shape of the impurity decomposing agent is not particularly limited but is preferably in the particulate form. In the case where the iron oxide and the alkaline earth metal compound are in the particulate form, the average particle size before the blending thereof, namely, before the formation of an impurity decomposing agent, is preferably 100 μm or less, more preferably 10 μm or less, still more preferably 1 μm or less. The average particle size is preferably from 0.01 to 100 μm, more preferably from 0.01 to 10 μm, still more preferably from 0.01 to 1 μm.

When the average particle size of each particle of iron oxide and alkaline earth metal compound is 100 μm or less, an octafluoropropane having higher purity can be obtained as well as the purification can be efficiently performed. This is presumed because the iron oxide and the alkaline earth metal compound each is a fine particle, therefore, the specific surface area thereof is increased and the iron oxide and the alkaline earth metal compound are readily dispersed with each other, as a result, the iron oxide and the alkaline earth metal compound are increased in the area and contact chance of the crude octafluoropropane with the impurity decomposing agent.

The concentration and the kind of impurities in the iron oxide and the alkaline earth metal compound are not particularly limited insofar as the ability of decomposing impurities in the crude octafluoropropane is not affected.

The shape of the impurity decomposing agent is not particularly limited, and in any shape, the impurity decomposing agent can be used for the purification, however, the impurity decomposing agent is preferably a granule in the particle form. Specific examples of this granule include pellet form and spherical form. The average particle size of the granule is preferably from 0.5 to 10 mm, more preferably from 1 to 5 mm.

When the average particle size of the granule falls within the above-described range, the contact chance of the impurities with the impurity decomposing agent increases and the decomposition and removal of the impurities can be efficiently performed. If the average particle size of the impurity decomposing agent exceeds 10 mm, the surface area participating in the adsorption and diffusion of gas is relatively reduced and the diffusion rate is sometimes lowered. On the other hand, if the average particle size of the impurity decomposing agent is less than 0.5 mm, the surface area participating in the adsorption and diffusion is relatively increased and although the diffusion speed can be higher, when the amount of gas treated is increased, a large differential pressure sometimes results.

For preparing the impurity decomposing agent comprising the iron oxide and the alkaline earth metal compound, a powder of the iron oxide and a powder of the alkaline earth metal compound are mixed, and the production method of the impurity decomposing agent is not limited. In the production (granulation) of the granule, insofar as the blending ratio is in the above-described range, satisfactory granulation may be attained by adding water to the mixture. In the case where the particle size of the iron oxide or alkaline earth metal compound is slightly large, the granulation may be performed by adding a binder together with water. The kind and the amount of the binder are not limited and a known binder may be used insofar as it does not affect the performance of the obtained impurity decomposing agent. Examples of the inorganic binder include clay and gypsum, and examples of the organic binder include methyl cellulose, polyvinyl alcohol and starch.

This granular impurity decomposing agent can be prepared by mixing the iron oxide and the alkaline earth metal compound, adding an appropriately amount of water, kneading the mixture and granulating the kneaded preform.

The kneader necessary for the preparation of such a granule may have a structure where the mixing and the granulation can be performed at the same time or where the mixing and the granulation are performed separately. Examples of the kneader where the mixing and granulation are performed at the same time include Henschel mixer and vertical mixer. It is also possible to perform the mixing in the Henschel mixer or V-type mixer and perform the granulation in a pan-type pelletizer or a drum pelletizer.

The thus-obtained granule is preferably dried at 100 to 150° C. for 3 to 5 hours in an inert gas stream such as air and nitrogen so as to elevate the hardness and evaporate the water content. The water content in the impurity decomposing agent after drying may be sufficient if the loss in weight after the drying at 110° C. for 2 to 3 hours in an air dryer is 1% by mass or less.

By using this impurity decomposing agent, the impurities in the crude octafluoropropane, such as fluorocarbon, are deemed to react with the alkaline earth metal compound in the impurity decomposing agent and thereby decompose. More specifically, the impurity CFC-115 reacts with a hydroxide, an oxide or a carbonate of an alkaline earth metal in the impurity decomposing agent to produce a fluoride and a chloride of alkaline earth metal and at the same time, produce carbon monoxide, water and the like. The carbon monoxide and water produced in this reaction process react using the iron as a catalyst to further produce hydrogen or methane. These reactions are presumed to continuously proceed, whereby the chlorine in CFC-115 is displaced with the produced hydrogen to produce pentafluoroethane (hereinafter sometimes referred to as "HFC-125"). By the same reaction mechanism, FC-1114 is produced from CFC-115. More specifically, it is presumed that HFC-125 is produced from CFC-115 and as a result of elimination of HF from HFC-125, FC-1114 is produced. These fluorocarbons obtained have a molecule size smaller than that of CFC-115 (molecule size: from 4.3 to 5.6 Å). For example, the molecule size of HFC-125 is from 3.4 to 4.9 Å and molecule size of FC-1114 is from 3.5 to 4.9 Å. As such, the molecular size difference between octafluoropropane (4.9 to 6.1 Å) and HFC-125 becomes significant as compared to the molecular size difference between octafluoropropane and CFC-115, and therefore, these impurities seems to be easily removed by the contact with an adsorbent subsequent to the contact with the impurity decomposing agent. Incidentally, the octafluoropropane is a relatively stable compound and therefore, does not decompose by the contact with the impurity decomposing agent under the heating temperature of 250 to 380° C.

Adsorbent

In the purification process of the present invention, the crude octafluoropropane is further contacted with an adsorbent after the contact with the impurity decomposing agent under elevated temperature.

The adsorbent used here may be a known adsorbent. Examples of the adsorbent which can be preferably used include activated carbon, zeolite (molecular sieve) and molecular sieving carbon. The activated carbon or molecular sieving carbon may be subjected to a pre-treatment before use, such as acid treatment, heat treatment and steam treatment.

Among these, molecular sieve having a pore size of 4 to 7 Å and molecular sieving carbon are preferred, and molecular sieving carbon 5A is more preferred.

The adsorbent may also be a commercially available product.

These adsorbents may be used individually or in combination of a plurality of adsorbents.

Purification Process for Crude Octafluoropropane

The purification process for octafluoropropane according to present invention comprises a step of contacting a crude octafluoropropane containing impurities with an impurity decomposing agent under elevated temperature (heating) (purification step 1) and a step of further contacting it with an adsorbent (purification step 2). The crude octafluoropropane to which the present invention can be applied may be either a product produced by a known method or a product available on the market.

(Purification Step 1)

With respect to the operation for the decomposition reaction of impurities such as fluorocarbon in a crude octafluoropropane, for example, the impurity decomposing agent is filled in a decomposition reactor and a crude octafluoropropane is fed to this decomposition reactor to contact the crude octafluoropropane with the impurity decomposing agent. The contacting step is not particularly limited, however, for example, a continuous operation by a flow method using a fixed bed is preferably used.

As for the reaction pressure, a pressure may or may not be applied and the treatment may be usually performed under a pressure easy to handle, however, the reaction is preferably performed at a pressure, in terms of the gauge pressure, from 0 to 2 MPa, more preferably on the order from 0 to 1 MPa.

The size (volume) of the decomposition reactor and the space velocity are not particularly limited insofar as the crude octafluoropropane and the impurity decomposing agent can contact for a certain time period, however, these are preferably set such that the residence time of the crude octafluoropropane in the decomposition reactor is from 1 to 30 seconds, more preferably from 4 to 30 seconds.

The decomposition reaction temperature in the decomposition reactor is preferably from 250° C. to 380° C., more preferably from 280° C. to 360° C. When the decomposition reaction temperature falls within this range, the impurity decomposing agent can maintain its activity. If the decomposition reaction temperature is less than 250° C., the activity of the impurity decomposing agent is not promoted and the decomposition rate is slow, whereas if the decomposition reaction temperature exceeds 380° C., the impurity decomposing agent itself decomposes due to heat and the decomposition of impurities in the crude octafluoropropane may not proceed.

(Purification Step 2)

The impurities after the purification step 1 are contacted further with an adsorbent and thereby substantially removed, whereby high-purity octafluoropropane can be obtained.

The adsorption operation can be performed, for example, by filling the adsorbent into an adsorption tower and feeding thereto the crude octafluoropropane after the decomposition reaction. In this case, the adsorption operation method is not limited and a known method may be used, for example, a continuous operation by a flow method using a fixed bed is preferably used.

In contacting the crude octafluoropropane passed through the purification step 1 with the adsorbent, either a gas phase or a liquid phase may be used. The linear velocity is preferably, in the case of a gas phase contact method, from 1 to 10 m/min, more preferably from 1 to 5 m/min, and in the case of a liquid phase contact method, preferably from 0.2 to 5 m/Hr, more preferably from 0.5 to 2 m/Hr.

The treatment can be usually performed at a pressure easy to handle and a particular operation such as application of a pressure is not necessary. In general, the pressure is preferably from 0 to 2 MPa in terms of gauge pressure.

The temperature at the adsorption operation may be usually about room temperature and heating or cooling is not necessary.

When the adsorption capability of the adsorbent is saturated, the adsorbent may be regenerated and used. In this case, the regeneration of the adsorbent is performed by passing various inert gases such as nitrogen gas heated to a high temperature through the adsorbent and thereby desorbing octafluoropropane and impurities such as fluorocarbon.

At the regeneration, the temperature of the inert gas is, in the case of a zeolite-base adsorbent, preferably from 20° C. to 600° C. and in the case of activated carbon or molecular sieving carbon-base adsorbent, preferably from 100° C. to 400° C.

[Process for Preparing Octafluoropropane]

In the process for preparing octafluoropropane, a crude octafluoropropane is produced and then the above-described purification process is applied thereto. More specifically, after the production of a crude octafluoropropane, the above-described purification step 1 and purification step 2 are performed.

The method for preparing the crude octafluoropropane is not limited, and a known method may be employed. As described above, a crude octafluoropropane can be produced by a known method, for example, by a method of electrolytically fluorinating 1-chloropropane (see, U.S. Pat. No. 3,709,800), a method of reacting trifluoropentachloropropane with manganese trifluoride (see, U.S. Pat. No. 2,578,721) or a method of reacting hydrogen fluoride and chlorine with compounds such as propane and propylene (see, U.S. Pat. No. 5,220,083).

To prepare the crude octafluoropropane containing impurities, a method of fluorinating a hexafluoropropene can be employed. For example, the crude octafluoropropane can be produced by known methods such as a method of reacting FC-1216 and fluorine gas under dilution with an inert gas and a reaction product gas, a method of electrically fluorinating FC-1216 in hydrogen fluoride (see, JP-B-62-61115) and a method of reacting at least one high-valence metal fluoride selected from cobalt trifluoride, manganese trifluoride and silver difluoride with FC-1216 (see, JP-B-62-54777).

The thus-produced crude octafluoropropane is subjected to the above-described purification step 1 and purification step 2, whereby octafluoropropane from which impurities are substantially removed can be obtained.

[High-Purity Octafluoropropane]

By using the purification process of the present invention, impurities in a crude octafluoropropane, such as fluorocarbon, particularly chloropentafluoroethane (CFC-115), a hexafluoropropene (FC-1216), dichlorodifluoromethane (CFC-12), chlorotrifluoromethane (CFC-13) and chlorodifluoromethane (HCFC-22), can be effectively removed. In particular, chlorine compounds as impurities difficult to remove by conventional purification methods, such as CFC-115, CFC-12, CFC-13 and HCFC-22, can be substantially removed and a high-purity octafluoropropane can be obtained.

The above-described impurities is usually contained in a crude octafluoropropane in an amount of 10 to 10,000 ppm by mass and when the purification process of the present invention is used, these impurities contained in an octafluoropropane can be removed to less than 1 ppm by mass (0.0001% by mass) and the purity of octafluoropropane obtained after the purification can be made 99.9999% by mass or more.

Here, the purity of octafluoropropane is defined as a value obtained by subtracting the fluorocarbon content other than octafluoropropane from 100% by mass. The analysis of an octafluoropropane product having a purity of 99.9999% by mass or more can be performed by (1) gas chromatography (GC) using TCD method, FID method (each including precut method) or ECD method and (2) gas chromatography-mass spectrometer (GC-MS).

[Uses]

Since impurities are substantially removed, the octafluoropropane obtained by the process of the present invention can be used as an etching gas in the etching step of a semiconductor device.

More specifically, in the production of a semiconductor device such as LSI and TFT, the octafluoropropane is suitably used as an etching gas for forming a circuit pattern from a thin or thick film formed by a CVD method, a sputtering method or a vapor deposition method.

The octafluoropropane can also be used as a cleaning gas in the cleaning step of a semiconductor device.

More specifically, in the apparatus for forming a thin or thick film, cleaning is performed to remove unnecessary deposits accumulated on the inner wall of apparatus and jig, because unnecessary deposits cause generation of particles and must be removed to obtain a good-quality film. The octafluoropropane according to the present invention can be suitably used as a cleaning gas for this purpose.

The gas according to the present invention comprises the high-purity octafluoropropane. This gas may be the pure octafluoropropane or in addition, may appropriately contain other gases. Examples of these other gases include He, Ne, Ar and $O_2$. The amount of these other gases blended is not particularly limited and in the case of using the high-purity octafluoropropane according to the present invention as an etching or cleaning gas, the amount blended varies depending on the kind of compound and thickness to be etched and can be selected according to the amount and thickness of the deposits to be cleaned.

Effects of the Invention

According to the process for purifying or preparing an octafluoropropane of the present invention, the impurities such as chlorine compounds, which have been heretofore difficult to remove, can be substantially removed and a high-purity octafluoropropane can be easily obtained. Furthermore, the octafluoropropane obtained by the purification process of the present invention is substantially free of impurities and therefore, can be effectively used as an etching or cleaning gas for use in the production process of a semiconductor device and the like.

EXAMPLES

The present invention is described in greater detail below by referring to Examples, however, the present invention should not be construed as being limited to these Examples.

Examples 1 to 3

[Preparation of Crude Octafluoropropane]

The octafluoropropane was prepared by the method of reacting FC-1216 with a high-valence metal fluoride.

The cobalt chloride was formed into a tablet (5 mm$\phi$×5 mm) and fluorinated with HF gas and then with $F_2$ gas to prepare $CoF_3$. 480 g of the $CoF_3$ obtained was filled in a nickel-made reactor (100 mm$\phi$×1,000 mm) and FC-1216 was introduced into the reactor by a flow method at a reaction temperature of 270° C. under atmospheric pressure. The crude octafluoropropane produced by the reaction was collected and the amount of impurities were determined by gas chromatography. The analysis conditions in the gas chromatography are shown below.

Instrument Body:

GC-14B (manufactured by Shimadzu Seisakusho K. K.)

Carrier: He

Detector: Hydrogen flame ionization detector (FID)

Amount of sample: 0.2 ml

Method of determination: Absolute calibration curve method

As a result of the analysis, the impurities in the crude octafluoropropane obtained were as follows: CFC-115 was 770 ppm by mass, FC-1216 was 200 ppm by mass, CFC-13 was 20 ppm by mass, and CFC-12 and HCFC-22 each was 10 ppm by mass.

[Preparation of Impurity Decomposing Tube]

The impurity decomposing agent comprising an iron oxide and an alkaline earth metal compound was prepared as follow. The components were blended to have γ-FeOOH (produced by Ishihara Sangyo)/Ca(OH)$_2$ (produced by Yoshizawa Sekkai Kogyo)=30/70% by mass (Example 1), γ-Fe$_2$O$_3$ (produced by Toda Kogyo)/Ca(OH)$_2$=20/80% by mass (Example 2), or γ-FeOOH/CaCO$_3$ (produced by Okutama Kogyo)=20/80% by mass (Example 3). After adding water, each blend was granulated, dried at 105° C. for 2 hours and sieved to prepare granules having a particle size of 0.85 to 2.8 mm. Thereafter, 1.9 g of each impurity decomposing agent was filled into a stainless steel tube (reaction tube) having an inner diameter of 16 mm to a layer height of 8 cm (volume: 15 ml) and treated in a nitrogen stream at 300° C. for 3 hour or more to prepare an impurity decomposition tube containing an impurity decomposing agent.

[Preparation of Adsorption Tower]

MSC-5A (trade name, produced by Ajinomoto Fine Techno) was used as the adsorbent. 71 g of MSC-5A as the adsorbent was filled into a stainless steel tube having an outer diameter of ½ inch (adsorption tower: 11 mm (inner diameter)×150 cm (tower length), volume: 130 ml) and treated in an nitrogen stream at 60° C. for 1 hour and at 160° C. for 7 hours, in total for 8 hours. The adsorption tower having the adsorbent was connected to the end of the impurity decomposition tube filled with the impurity decomposing agent.

[Purification of Crude Octafluoropropane]

The previously prepared crude octafluoropropane in a gas phase was passed under a pressure of 0.7 MPa at a space velocity of 650 $Hr^{-1}$ through the impurity decomposition tube and at a linear velocity of 1 m/min through the adsorption tower. The decomposition reaction temperature in the impurity decomposition tube was 350° C. The octafluoropropane passing through the impurity decomposition tube and the octafluoropropane passing through the adsorption tower were collected, respectively, and were determined by gas chromatography under the above-described conditions.

In Example 1, the contents of impurities such as fluorocarbon contained in the octafluoropropane at the outlet of the impurity decomposition tube and in the octafluoropropane at the outlet of the adsorption tower were analyzed after 2 hours, 5 hours and 10 hours since the octafluoropropane started flowing. The results obtained are shown in Table 3.

As a result of this analysis, out of the impurities such as fluorocarbon contained in the inlet gas, CFC-115, FC-1216, CFC-12, CFC-13 and HCFC-22 were scarcely detected at the outlet of the impurity decomposition tube, and HFC-125 and FC-1114 were detected. The impurities (decomposition product) such as fluorocarbon at the outlet of the impurity decomposition tube can be removed by adsorption. Thus, it was verified that CFC-115, FC-1216, CFC-12, CFC-13 and HCFC-22 in octafluoropropane can be removed.

The change in the concentration of CFC-115 contained in octafluoropropane at the outlet of the adsorption tower after 2 hours and 5 hours since the octafluoropropane started flowing and the removal amount of CFC-115 until the break through are shown in Table 6. Here, the break through was set to the point where 1 ppm by mass of impurities such as fluorocarbon were detected at the adsorption tower outlet and the amount of CFC-115 flown until the break-through was used as the removal amount of CFC-115.

Also in the case of using $\gamma$-$Fe_2O_3$ as the ferric oxide (Example 2) and using $CaCO_3$ as the alkaline earth metal compound (Example 3), an excellent effect of removing CFC-115 was exerted and this reveals that octafluoropropane can be purified to high purity.

TABLE 3

Change in Concentration of Each Impurity With Passage of Time at Impurity Decomposition Tube Outlet and Adsorption Tower Outlet (Example 1)

| | Time (Hr) | Change in Concentration of Each Impurity (ppm by mass) | | | | | | |
|---|---|---|---|---|---|---|---|---|
| | | CFC-115 | FC-1216 | CFC-12 | CFC-13 | HCFC-22 | HFC-125 | FC-1114 |
| Sample fed | | 770 | 200 | 10 | 20 | 10 | 0 | 0 |
| Impurity decomposition tube outlet | 2 | 0 | 0 | 0 | 0 | 0 | 3 | 0 |
| | 5 | 0 | 0 | 0 | 0 | 0 | 108 | 0 |
| | 10 | 0 | 0 | 0 | 0 | 0 | 13 | 16 |
| Adsorption tower outlet | 2 | 0 | 0 | 0 | 0 | 0 | 0 | 0 |
| | 5 | 0 | 0 | 0 | 0 | 0 | 0 | 0 |
| | 10 | 0 | 0 | 0 | 0 | 0 | 0 | 0 |

Comparative Example 1

An adsorption removal test of impurities such as fluorocarbon in octafluoropropane was performed in the same manner as in Example 1 except that the decomposition step of impurities such as fluorocarbon was omitted in Example 1. The concentrations of impurities before and after the passing through MSC-5A as the adsorbent were determined in the same manner as in Example 1 by gas chromatography.

The change in the concentration of impurities such as fluorocarbon contained in octafluoropropane at the outlet of the adsorption tower after 1 hour, 5 hours and 10 hours since the octafluoropropane started flowing are shown in Table 4. As for CFC-115, the break-through occurred almost at the same time with the start of flowing of octafluoropropane, revealing that CFC-115 is not removed by adsorption only by the adsorbent. Also, CFC-12, CFC-13 and HCFC-22 all had the break-through within 5 to 10 hours and it is revealed that the adsorption removing ability is low.

The removal amount of FC-1216 by the purification process of the present invention (Example 1) and the removal amount of FC-1216 only by the adsorption purification (Comparative Example 1) are shown in Table 5. By setting the break-through to the point when FC-1216 in octafluoropropane was detected in a concentration of 1 ppm by mass at the outlet of adsorption tower, the amount of FC-1216 flown until the break-through was used as the removal amount. Although it is seen from the results of Example 1 and Comparative Example 1 that FC-1216 can be removed by the adsorption, whether FC-1216 itself is decomposed when the decomposition step is provided before the adsorption step as in Example 1 is not known. However, since FC-1216 is already removed, the removal amount thereof is elevated as compared with the conventional adsorption purification and it is revealed that the purification process of the present invention is more effective.

TABLE 4

Change in Concentration of Each Impurity at Adsorption Tower Outlet (Comparative Example 1)

| Time Passed | Change in Concentration of Each Impurity (ppm by mass) | | | | |
|---|---|---|---|---|---|
| (Hr) | CFC-115 | FC-1216 | CFC-12 | CFC-13 | HCFC-22 |
| Sample fed | 700 | 200 | 10 | 20 | 10 |
| 1 | 39 | 0 | 0 | 0 | 0 |
| 5 | 487 | 0 | 5 | 4 | 0 |
| 10 | 700 | 0 | 10 | 15 | 5 |

TABLE 5

Removal Amount of FC-1216

| | Removal Amount of FC-1216 (mg) |
|---|---|
| Example 1 | 400 |
| Comparative Example 1 | 210 |

Comparative Examples 2 to 4

Tests were performed under the same conditions as in Examples 1 to 3 except for using an impurity decomposing agent different from Examples 1 to 3.

The impurity decomposing agents used were γ-FeOOH=100% by mass (Comparative Example 2), γ-$Fe_2O_3$=100% by mass (Comparative Example 3) and Ca(OH)$_2$=100% by mass (Comparative Example 4), and through each impurity decomposing agent, the same octafluoropropane as in Examples 1 to 3 was passed. The break-through was set to the point when fluorocarbon impurity in octafluoropropane was detected in a concentration of 1 ppm by mass at the outlet of the adsorption tower.

The change in the concentration of CFC-115 contained in octafluoropropane at the outlet of the adsorption tower after 2 hours and 5 hours since the octafluoropropane started flowing and the removal amount of CFC-115 are shown in Table 6.

The impurity decomposing agent comprising only ferric oxide (Comparative Examples 2 and 3) could not keep the shape and probably because of this, the break-through of CFC-115 at the adsorption tower outlet occurred early. The decomposition reaction of FC-115 scarcely proceeded only with alkaline earth metal compound (Comparative Example 4) and the removal amount of FC-115 was very small. From these, it is seen that unless an impurity decomposing agent containing both ferric oxide and alkaline earth metal compound mixed at an appropriate ratio is used, CFC-115 is scarcely decomposed and good results cannot be obtained in the removal of CFC-115.

TABLE 6

Change in Concentration at Absorption Tower Outlet and removal amount of CFC-115 in Each Test

| | Composition of Impurity Decomposing Agent (% by mass) | | Time passed (Hr) | Change in Concentration of FC-115 (ppm by mass) | Removal Amount of FC-115 (mg) |
|---|---|---|---|---|---|
| | Sample fed | | | 770 | |
| Example 1 | γ-FeOOH | 30 | 2 | 0 | 705 |
| | Ca(OH)$_2$ | 70 | 5 | 0 | |
| Example 2 | γ-$Fe_2O_3$ | 20 | 2 | 0 | 600 |
| | Ca(OH)$_2$ | 80 | 5 | 0 | |
| Example 3 | γ-FeOOH | 20 | 2 | 0 | 585 |
| | CaCO$_3$ | 80 | 5 | 0 | |
| Comparative Example 1 | Only adsorbent (MSC-5A) | | 2 | 130 | 10 |
| | | | 5 | 355 | |
| Comparative Example 2 | γ-FeOOH | 100 | 2 | 60 | 85 |
| | | | 5 | 235 | |
| Comparative Example 3 | γ-$Fe_2O_3$ | 100 | 2 | 100 | 40 |
| | | | 5 | 295 | |
| Comparative Example 4 | Ca(OH)$_2$ | 100 | 2 | 110 | 15 |
| | | | 5 | 350 | |

Reference Examples 1 and 2

The tests were performed under the same conditions as in Example 1 except for the decomposition temperature. The decomposition temperature was 240° C. (Reference Example 1) and 400° C. (Reference Example 2).

The change in concentration of CFC-115 at the adsorption tower outlet after 2 hours, 5 hours and 10 hours since the octafluoropropane started flowing is shown in Table 7. As seen from the test results, the activity of the impurity decomposing agent was not promoted due to excessively low temperature of 240° C. and probably because of this, the decomposition of CFC-115 did not proceed. At an excessively high temperature of 400° C., the impurity decomposing agent itself was decomposed by the heat and the break-through of CFC-115 at the adsorption tower outlet occurred early. The removal amount of CFC-115 was about 10 mg in both of Reference Examples 1 and 2, revealing that the removal amount is small.

TABLE 7

Change in Concentration of CFC-115 at Adsorption Tower Outlet with respect to Decomposition Temperature

| Time Passed (Hr) | Change in Concentration of CFC-115 (ppm by mass) | | |
|---|---|---|---|
| | Example 1 (350° C.) | Reference Example 1 (240° C.) | Reference Example 2 (400° C.) |
| Sample fed | 770 | 770 | 770 |
| 2 | 0 | 350 | 260 |
| 5 | 0 | 530 | 500 |
| 10 | 0 | 700 | 700 |

What is claimed is:

1. A process for purifying an octafluoropropane, comprising the step of contacting a crude octafluoropropane containing impurities with an impurity decomposing agent under elevated temperature and then with an adsorbent to substantially remove said impurities from said crude octafluoropropane,
   wherein said impurity decomposing agent comprises an iron oxide and an alkaline earth metal compound.

2. The process for purifying an octafluoropropane as claimed in claim 1, wherein said iron oxide is ferric oxide.

3. The process for purifying an octafluoropropane as claimed in claim 2, wherein said ferric oxide is γ-iron hydroxide oxide and/or γ-ferric oxide.

4. The process for purifying an octafluoropropane as claimed in any one of claims 2 to 3, wherein said alkaline earth metal compound is at least one compound selected from the group consisting of oxides, of an alkaline earth metal, hydroxides of an alkaline earth metal and carbonates of an alkaline earth metal, wherein the alkaline earth metal is selected from the group consisting of magnesium, calcium, strontium and barium.

5. The process for purifying an octafluoropropane as claimed in claim 1, wherein said impurity decomposing agent contains from 5 to 40% by mass of an iron oxide and from 60 to 95% by mass of an alkaline earth metal compound based on the entire mass of said impurity decomposing agent.

6. The process for purifying octafluoropropane as claimed in claim 1, wherein said impurity decomposing agent is a granule comprising a powder of said iron oxide having an average particle size of 100 μm or less and a powder of said alkaline earth metal compound having an average particle size of 100 μm or less.

7. The process for purifying an octafluoropropane as claimed in claim 1, wherein said impurity decomposing agent is a granule having an average particle size of 0.5 to 10 mm.

8. The process for purifying an octafluoropropane as claimed in claim 1, wherein said crude octafluoropropane is contacted with said impurity decomposing agent at a temperature of 250 to 380° C.

9. The process for purifying an octafluoropropane as claimed in claim 1, wherein said adsorbent is at least one member selected from the group consisting of activated carbon, molecular sieve and molecular sieving carbon.

10. The process for purifying an octafluoropropane as claimed in claim 1, wherein said crude octafluoropropane contains said impurities in an amount of 10 to 10,000 ppm by mass.

11. The process for purifying an octafluoropropane as claimed in claim 10, wherein said impurity is at least one compound selected from the group consisting of chloropentafluoroethane, hexafluoropropene, chlorotrifluoromethane, dichlorodifluoromethane and chlorodifluoromethane.

12. The process for purifying an octafluoropropane as claimed in claim 11, wherein after the impurities are substantially removed, the concentration of impurities remaining in the octafluoropropane is less than 1 ppm by mass.

13. A process for preparing an octafluoropropane, comprising the steps of producing a crude octafluoropropane containing impurities, and contacting said crude octafluoropropane with an impurity decomposing agent under elevated temperature and then with an adsorbent to obtain an octafluoropropane from which impurities are substantially removed, wherein said impurity decomposing agent comprises an iron oxide and an alkaline earth metal compound.

14. The process for preparing an octafluoropropane as claimed in claim 13, wherein the step of producing an octafluoropropane containing impurities is a fluorination of hexafluoropropene.

15. The process for preparing an octafluoropropane as claimed in claim 13 or 14, wherein said impurity is at least one compound selected from the group consisting of chloropentafluoroethane, hexafluoropropene, chlorotrifluoromethane, dichlorodifluoromethane and chlorodifluoromethane.

* * * * *